United States Patent [19]

Baboian et al.

[11] 4,147,596
[45] Apr. 3, 1979

[54] METHOD AND APPARATUS FOR MONITORING THE EFFECTIVENESS OF CORROSION INHIBITION OF COOLANT FLUID

[75] Inventors: Robert Baboian, Johnston, R.I.; Gardner S. Haynes, Attleboro, Mass.

[73] Assignee: Texas Instruments Incorporated, Dallas, Tex.

[21] Appl. No.: 866,074

[22] Filed: Dec. 30, 1977

[51] Int. Cl.² .............. G01N 27/46; F01P 5/14
[52] U.S. Cl. .................... 204/1 T; 123/41.15; 324/65 CP; 204/195 C; 340/59
[58] Field of Search ........... 204/1 C, 195 C; 324/29, 324/71 R, 65 CP; 73/86; 123/41.15; 340/59

[56] References Cited

U.S. PATENT DOCUMENTS

| | | | |
|---|---|---|---|
| 3,197,388 | 7/1965 | Marsh et al. | 204/1 C |
| 3,649,472 | 3/1972 | Morrissey et al. | 204/1 T |
| 3,725,212 | 4/1973 | Kawamoto et al. | 204/1 T |
| 3,748,247 | 7/1973 | Weisstuch | 204/195 C |
| 3,832,982 | 9/1974 | Guehr | 123/41.15 |

OTHER PUBLICATIONS

A. Weisstuch et al, "Effectiveness of Cooling Water Treatments as Galvanic Corrosion Inhibitors," *Materials Protection Performance*, vol. 11, pp. 23-26 (1972).
M. S. Walker et al. "New Method Developed for Monitoring Automotive Cooling System Corrosion," *Materials Protection*, pp. 47-52 (1969).

*Primary Examiner*—Aaron Weisstuch
*Attorney, Agent, or Firm*—John A. Haug; James P. McAndrews

[57] ABSTRACT

A sensor is adapted to be mounted so that it comes in contact with coolant fluid of a vehicular cooling system. When the corrosion inhibiting characteristic of the fluid is effective to prevent corrosion a first potential range is produced whereas when the characteristic is ineffective a second range exists. The effectiveness of the inhibiting characteristic can be displayed in the form of a high impedance voltmeter mounted in the dashboard or other convenient location or indicating means such as a light can be actuated when the potential reaches a threshold level indicating that the inhibiting characteristic is not effective to prevent corrosion. The sensor comprises a reference electrode used with a single sensor electrode on one embodiment and with a pair of sensor electrodes in a second embodiment.

10 Claims, 8 Drawing Figures

METHOD AND APPARATUS FOR MONITORING THE EFFECTIVENESS OF CORROSION INHIBITION OF COOLANT FLUID

This invention relates generally to vehicular cooling systems and more particularly to monitoring the effectiveness of the corrosion inhibiting characteristic of coolant fluid used in such systems.

Vehicular cooling systems are composed of several components including the radiator, circulating pump, passages in the motor block and associated tubing. Since the system is composed of metallic parts there is a need to prevent or at least mitigate corrosion in order to prolong the useful life of the system. To this end it has become common practice to add chemical substances to the coolant fluid which tend to inhibit corrosion of the metal surfaces which come in contact with the fluid. Such substances are known as inhibitors and generally form a film on the metal surfaces thereby protecting them from degradation. Thus, commercially available permanent antifreeze includes an inhibitor which is highly successful in preventing corrosion; however, over the course of time the corrosion inhibiting characteristic of the fluid can become less effective due to chemical decomposition of the inhibitor, leakage or boiling of the coolant fluid with subsequent replenishment with water. It is therefore recommended procedure to periodically change the coolant fluid with fresh permanent antifreeze. This of course can be wasteful if the corrosion inhibiting characteristic of the coolant fluid is still effective. On the other hand the tendency to employ aluminum radiators in some automobiles has exacerbated the problem since aluminum radiators corrode much more quickly than conventional copper radiators.

It is an object of this invention to provide a method and apparatus to monitor the effectiveness of the corrosion inhibiting characteristic of coolant fluid. It is another object of this invention to provide a sensor which can be used in monitoring the inhibiting ability of the coolant fluid which is inexpensive, reliable and long lived. Yet another object is the provision of an output signal upon the debilitation of the corrosion inhibiting characteristic of the coolant fluid and to employ the signal to actuate a switch to provide visual or audible indication or to activate an inhibitor replenishment means.

Other objects, advantages and details of the method and apparatus provided by this invention appear in the following detailed description of preferred embodiments of the invention, the detailed descriptions referring to the drawings in which.

Figure 1:
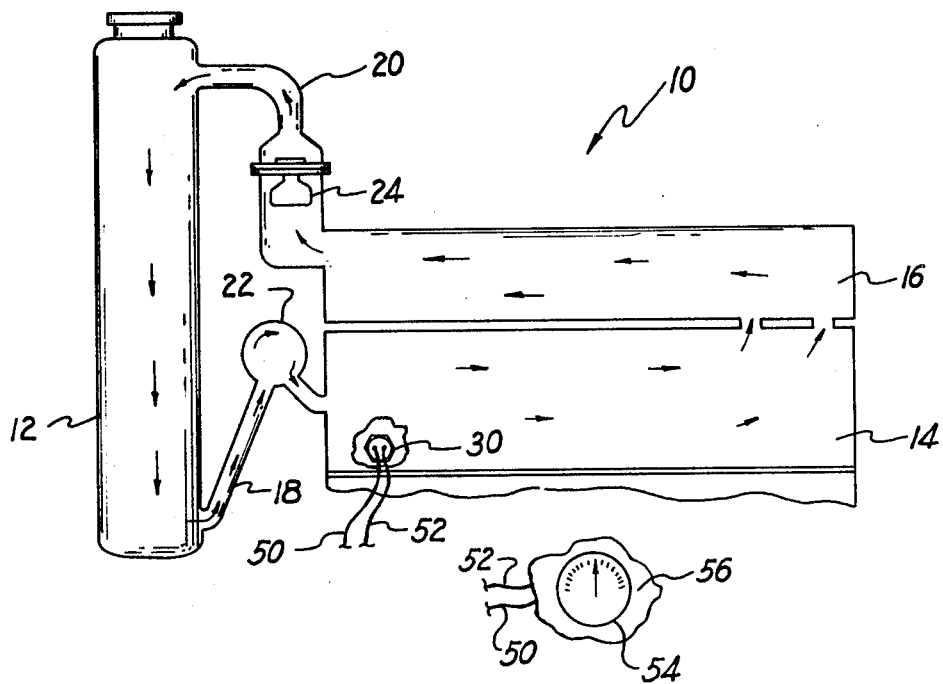
FIG. 1 is a schematic side elevation of a vehicular cooling system in which a sensor is mounted to monitor the effectiveness of the inhibiting characteristic of the coolant fluid and a meter is mounted in the dashboard to provide visual indication of such effectiveness.

Briefly, in accordance with the invention the effectiveness of the corrosion inhibiting characteristic of the coolant fluid, particularly with respect to aluminum radiators, is monitored and measured by means of a potential measuring circuit employing an electrochemical reference electrode and a pair of electrochemical sensing electrodes electrically connected to one another and placed in contact with the coolant fluid. When the inhibiting characteristic is effective a first range of electrical potential exists between the reference and sensing electrodes; however, when the inhibiting characteristic becomes ineffective for any reason a second range of electrical potential exists therebetween. Thus, when the potential reaches a threshold level as it moves into the second range visual or auditory indicating means can be activated or a continuous read out as with a voltmeter can be provided.

Referring to the drawings, 10 indicates a vehicular cooling system comprising a radiator 12, cylinder block 14, cylinder head 16, tubing lines 18 and 20 connecting the radiator respectively to block 14 and head 16, circulating pump 22 in line 18 and thermostat 24 on line 20. It will be appreciated that as described the system conforms to a conventional cooling system in use in motor vehicles. Sensor 30 extends through the wall of cylinder block 14 (see FIG. 1 and FIG. 3) so that its distal end is adapted to come in contact with the coolant fluid circulating in the system. The darts shown in FIG. 1 indicate the circulation of the coolant liquid. As seen in FIG. 2, sensor 30 comprises a tubular housing having a bore 32 extending along its longitudinal axis and is provided with a threaded portion 34 to enable it to be mounted in a complimentary threaded bore. Head 36 may be hexagonally configured to facilitate insertion in bore 38 of the cylinder block wall. First and second electrode wires 40, 42 are mounted in bore 32 of the sensor and maintained in spaced relation to each other and to the wall of bore 32 by any conventional electrically insulative potting material 44 which is non reactive with the cooling fluid. Electrodes 40 and 42 extend beyond distal end 46 of sensor 30 so that they will be inundated by the coolant fluid. Electrodes 40, 42 are connected to a high impedance voltmeter 54 which is conveniently mounted in dash 56 of the vehicle.

Figure 4:
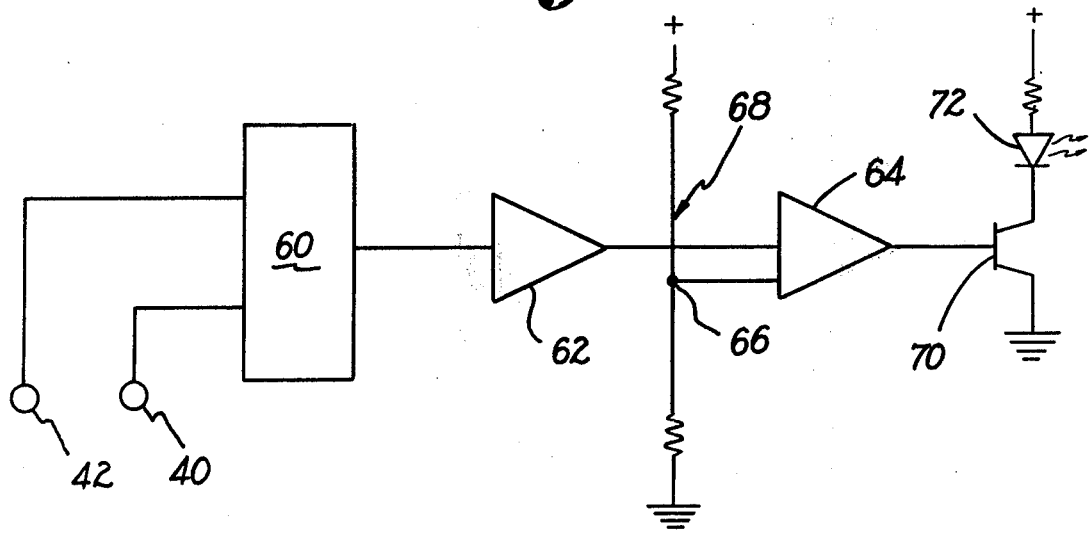
FIG. 4 is a schematic electrical circuit useful with the FIG. 2 sensor.

As seen in FIG. 4, the effectiveness of the inhibitor can be monitored employing a potential measuring circuit comprising a high impedance voltage follower 60, which receives inputs from electrode 40, 42 coupled to amplifier 62 which in turn is coupled to voltage comparator 64. The threshold of comparator 64 is set at junction 66 of voltage divider 68. Comparator 64 is coupled to the base of NPN transistor 70 whose collector is coupled to light emitting diode 72.

The particular configuration of sensor 30 is a matter of choice as long as it disposes spaced first and second electrodes in contact with the coolant fluid. Further, although the electrodes are shown to be in wire form it will be appreciated that other electrode configurations are within the purview of the invention. The first electrode, element 40, serves as a reference electrode and may be any standard commercial reference electrode such as the calomel family, the silver family including Ag/Ag halide and Ag/AgO, the copper family such as Cu/Cu halide and Cu/CuSO$_4$ or other stable reference electrode. In some cases metallic silver exposed to the coolant liquid can be used as a reference potential since the metal is in contact with the oxide and a stable reference potential exists.

It has been found that the second electrode element 42 can be composed of low carbon steel, copper, nickel, zinc, titanium, columbium, platinum, gold, lead and tin. The demarcation between the two ranges of potentials indicating effective and ineffective corrosion inhibiting characteristics varies among the materials with a particularly good demarcation existing for steel. As seen in Table I in which reference electrode 40 is a fine silver wire and the second electrode 42 is either (a) steel, or (b) copper, a threshold level of −0.300 volts will be very effective in providing the desired indication of effectiveness of the inhibiting characteristic for steel vs. silver electrode.

TABLE I

| | | a (volts) | b (volts) |
|---|---|---|---|
| 1. | H$_2$O | −0.720 | −0.035 |
| 2. | 15% solution with H$_2$O of ethylene-glycol | −0.690 | +0.039 |
| 3. | 30% solution with H$_2$O of ethylene-glycol | −0.698 | +0.080 |
| 4. | 50% solution with H$_2$O of ethylene-glycol | −0.670 | +0.090 |
| 5. | 15% solution with H$_2$O of permanent anti-freeze | −0.236 | −0.110 |
| 6. | 30% solution with H$_2$O of permanent anti-freeze | −0.210 | −0.186 |
| 7. | 50% solution with H$_2$O of permanent anti-freeze | −0.185 | −0.110 |

The data included in Table I was obtained using a reference electrode of silver and an electrode of steel for column (a) and copper for column (b), and DuPont de Nemours "Telar" antifreeze.

The potential of steel in different commercially available antifreezes is shown in Tables IIa and b. The particular antifreezes are identified as follows:

| Brand Name | Distributor | Identification |
|---|---|---|
| A Zerex | PPG Industries, Inc. | — |
| B Ford | Ford Marketing Corporation | 8A-19549-A |
| C Prestone II | Union Carbide Corporation | AF-542 |
| D Dowgard | Dow Chemical Company | D675 |
| E Pennzoil | Pennzoil Company, Oil City PA | — |
| F Shellzone | Shell Oil Company | — |
| G Mac's Radicool | Mac's Super Gloss Co. Inc. | #1800 |
| H Pah-nol | Houghton Chemical Corp. | — |

Typically, inhibitors in commercial antifreezes include varying percentages of borate, phosphate, nitrate, silicate and mercaptobenzothiazole.

TABLE IIa

| | Potential of Steel Electrode 42 in Antifreeze Solutions (25%) | | |
|---|---|---|---|
| Type | Reference Electrode 40 Ag (volts) | Reference Electrode 40 SCE (volts) | Reference Electrode 40 Ag/AgCl (volts) |
| Tap Water | −0.581 | −0.520 | −0.645 |
| 25% Ethylene Glycol (No Inhibitor) | −0.550 | −0.510 | −0.590 |
| A | −0.210 | −0.245 | −0.390 |
| B | −0.160 | −0.280 | −0.275 |
| C | −0.205 | −0.285 | −0.295 |
| D | −0.205 | −0.280 | −0.285 |
| E | −0.230 | −0.350 | −0.300 |
| F | −0.190 | −0.320 | −0.310 |
| G | −0.135 | −0.200 | −0.250 |

TABLE IIb

| | Potential of Steel Electrode 42 in Antifreeze Solutions (50%) | | |
|---|---|---|---|
| Type | Reference Electrode 40 Ag (volts) | Reference Electrode 40 SCE (volts) | Reference Electrode 40 Ag/AgCl (volts) |
| Tap Water | −0.581 | −0.520 | −0.645 |
| 50% Ethylene Glycol (No Inhibitor) | −0.520 | −0.590 | −580 |
| A | −0.220 | −0.275 | −0.300 |
| B | −0.120 | −0.235 | −0.235 |
| C | −0.205 | −0.285 | −0.280 |
| D | −0.175 | −0.230 | −0.230 |
| E | −0.160 | −0.290 | −0.305 |
| F | −0.200 | −0.310 | −0.295 |
| G | −0.150 | −0.205 | −0.250 |

Table III shows the potential of steel in 25% ethylene glycol and 25% ethylene glycol plus commercial inhibitors at concentrations recommended by the manufacturer.

TABLE III

| Type | Reference Electrode 40 Ag (volts) | Reference Electrode 40 SEC (volts) | Reference Electrode 40 Ag/AgCl (volts) |
|---|---|---|---|
| None | −0.560 | −0.510 | −0.630 |
| k | −0.150 | −0.145 | −0.265 |
| None | −0.550 | −0.490 | −0.625 |
| l | −0.195 | −0.280 | −0.320 |
| None | −0.540 | −0.585 | −0.600 |
| m | −0.295 | −0.220 | −0.195 |
| None | −0.545 | −0.480 | −0.625 |
| n | −0.255 | −0.250 | −0.350 |

In Table III the brand name of the inhibitors are Shell Oil Company for k, Solder Seal for l, Prestone for m and Valvoline for n.

As mentioned above, the demarcation between the ranges of potentials indicating effective and ineffective corrosion inhibiting characteristics varies with different materials. Table Iva, b and c shows the potentials of a number of different electrode 42 metals versus a reference electrode 40 of Ag/AgCl for Table IVa, saturated calomel for Table IVb and silver wire for Table IVc.

TABLE IVa

| Metal | Tap Water (volts) | 25% Pahnol Antifreeze (volts) | 50% Pahnol Antifreeze (volts) |
|---|---|---|---|
| Steel | −0.645 | −0.330 | −0.247 |
| Nickel | −0.450 | −0.420 | −0.385 |
| Zinc | −1.098 | −0.940 | −0.756 |
| Copper | −0.157 | −0.020 | 0.000 |
| Titanium | −0.350 | −0.295 | −0.318 |
| Columbium | −0.416 | −0.215 | −0.171 |
| Gold | −0.226 | −0.075 | −0.098 |

TABLE IVa-continued

| Metal | Tap Water (volts) | 25% Pahnol Antifreeze (volts) | 50% Pahnol Antifreeze (volts) |
|---|---|---|---|
| Lead | −0.649 | −0.525 | −0.559 |

TABLE IVb

| Metal | Tap Water (volts) | 25% Pahnol Antifreeze (volts) | 50% Pahnol Antifreeze (volts) |
|---|---|---|---|
| Steel | −0.520 | −0.250 | −0.190 |
| Zinc | −0.920 | −0.825 | −0.690 |
| Titanium | −0.220 | −0.370 | −0.260 |
| Columbium | −0.160 | −0.155 | −0.110 |
| Gold | −0.090 | 0.000 | −0.030 |
| Lead | −0.545 | −0.430 | −0.506 |

TABLE IVc

| Metal | Tap Water (volts) | 25% Pahnol Antifreeze (volts) | 50% Pahnol Antifreeze (volts) |
|---|---|---|---|
| Steel | −0.581 | −0.260 | −0.138 |
| Nickel | −0.390 | −0.345 | −0.285 |
| Zinc | −1.035 | −0.830 | −0.654 |
| Copper | −0.086 | +0.045 | +0.124 |
| Titanium | −0.295 | −0.260 | −0.205 |
| Columbium | −0.287 | −0.120 | −0.058 |
| Gold | −0.110 | +0.005 | +0.005 |
| Lead | −0.635 | −0.415 | −0.448 |

From the above tables it will be seen that the most effective material for electrode 42 is steel while zinc, columbium and gold are acceptable. Lead, titanium, copper and nickel could be used but are not as effective as steel, zinc, columbium and gold and thus would require more sophisticated electrical circuitry for effective use.

Figure 2:
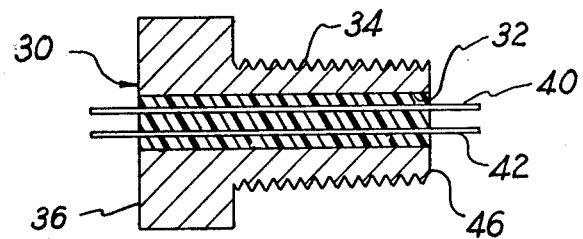
FIG. 2 is an enlarged cross sectional side elevational view of the FIG. 1 sensor.
Figure 3:
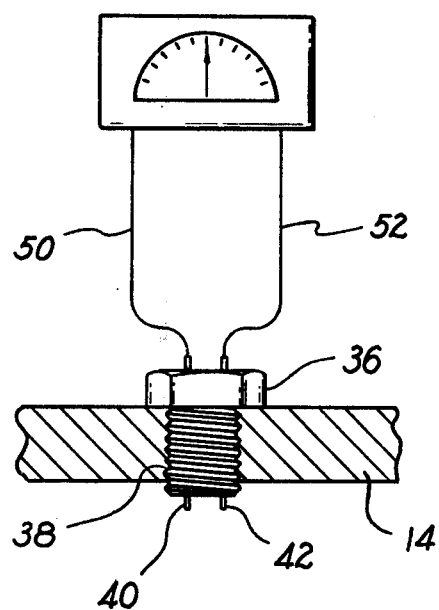
FIG. 3 is a cross sectional view of a portion of the cooling system wall showing the FIG. 2 sensor mounted therein and connected to a high impedance voltmeter.
Figure 5:
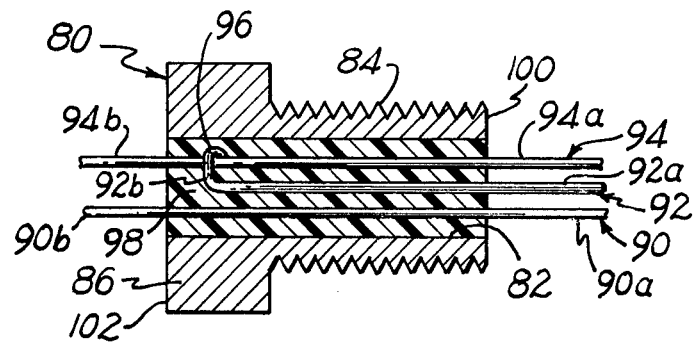
FIG. 5 is an enlarged cross sectional side elevational view similar to FIG. 2 of another embodiment of the sensor.

FIG. 5 shows a modification of the sensor shown in FIGS. 1-3 which is particularly useful for sensing the corrosivity of liquids used with aluminum radiator cooling systems. Sensor 80 comprises a tubular housing having a bore 82 extending along its longitudinal axis and is provided with a threaded portion 84 to enable it to be mounted in a complementary threaded bore. Head 86 may be hexagonally configured to facilitate insertion in a bore of the cylinder block wall in the same manner as sensor 30. A reference electrode 90, similar to electrode 40 of sensor 30, is disposed in bore 82 and extends generally parallel to the longitudinal axis of the tubular housing. Second and third electrodes, 92, 94 respectively form a pair of sensing electrodes, which may be referred to elsewhere as "dual" sensing electrodes and are also disposed in bore 82 and extend generally parallel to each other and to electrode 90 with one end of electrode 92 physically electrically connected to electrode 94 as indicated at 96 by any conventional means, as by soldering or welding. The three electrodes are fixed in position spaced from the wall defining bore 82 and each other, except for end 92b which is electrically connected in short circuit relation to electrode 94, by suitable electrically insulative potting material 98 which is non reactive with the cooling fluid. The electrodes extend beyond distal end 100 of sensor 80 so that they will be inundated by the coolant fluid. The opposite ends 90b and 94b of electrodes 90 and 94 respectively extend beyond distal end 102 of sensor 80 and serve to connect the sensor to a high impedance voltmeter, such as voltmeter 54 shown in FIG. 1.

As noted supra, aluminum radiators are highly susceptible to corrosion. Coolant solutions become corrosive to aluminum at levels of inhibitor concentration which may not be corrosive to other conventional cooling system materials such as copper and iron alloys. Thus, to be effective in monitoring protection against corrosion for aluminum, the sensor must be particularly sensitive to the specific corrosive conditions for the material. In order to determine its critical inhibitor concentration for prevention of corrosion, samples of aluminum were placed into a typical solution at several phosphate (inhibitor) concentrations and it was empirically found that the critical concentration for the solution was 0.035 molar phosphate. That is, at levels at and above 0.035 molar phosphate corrosion did not occur, while at levels below that level corrosion was noted.

The composition of the solution was as follows:

equal parts of glycol and water
0.005 molar $Na_2B_4O_7 \cdot 10 H_2O$
pH of 8.5
200 ppm of $Cl^-$
$Na_2HPO_4 \cdot 12H_2O$ in various concentrations as indicated
the pH was adjusted using NaOH
and the $Cl^-$ was added as NaCl.

Although attempts have been made to use aluminum as the sensing electrode in the sensor 30 configuration to determine when corrosion conditions occurred it was found to be too unstable. This may be seen in table Va below which gives the mean potentials in volts of aluminum versus an SCE reference electrode in the above solution and a range of plus or minus two standard deviations.

TABLE Va

| phosphate concentration | mean potential, V | +2SD | −2SD |
|---|---|---|---|
| 0.000M | −0.714 | −0.240 | −1.188 |
| 0.005M | −0.642 | −0.472 | −0.812 |
| 0.010M | −0.624 | −0.462 | −0.786 |
| 0.020M | −0.620 | −0.382 | −0.858 |
| 0.035M | −0.644 | −0.354 | −0.934 |
| 0.070M | −0.581 | −0.319 | −0.843 |

It will be observed that there is no clear line of demarcation in potentials which could be used to indicate a corrosive environment for aluminum, particularly in the vicinity of approximately 0.035M phosphate.

A steel sensing electrode, on the other hand, which is useful to indicate changes in the effectiveness of the corrosion inhibition characteristics of coolant fluid for various materials, exhibits a potential which changes when small amounts of phosphate inhibitor are added, as seen in table Vb, which gives the mean potentials of steel in volts versus a silver reference electrode for the same solutions as those used for table Va. Note the stability of the values as indicated by the plus or minus two standard deviations.

Table Vb

| phosphate concentration | mean potential, V | +2SD | −2SD |
|---|---|---|---|
| 0.000M | −0.373 | −0.255 | −0.491 |
| 0.005M | −0.207 | −0.129 | −0.285 |
| 0.010M | −0.171 | −0.079 | −0.263 |
| 0.020M | −0.153 | −0.043 | −0.263 |
| 0.035M | −0.094 | −0.006 | −0.182 |
| 0.070M | −0.096 | −0.014 | −0.178 |

It will be seen that when using steel as the sensing electrode the significant changes in potential occur at levels of phosphate addition which are too low to be effective in monitoring the effectiveness of corrosion protection of aluminum. For instance between 0.035M, the critical level for aluminum for the coolant solution employed, and 0.070M which is considered a fully inhibited solution, there is a decrease of 0.002 volts in the mean potential compared to an increase of 0.166 volts in the addition of phosphate up to the 0.005 M level. Thus, the change in potential of the steel electrode does not meet the requirements for monitoring the effectiveness of the corrosion inhibitor with regard to aluminum radiators.

In accordance with the embodiment depicted in FIG. 5, when one of the sensing electrodes 92, 94 is composed of aluminum and the other of steel, the result is a combined potential particularly sensitive in the range of 0.070 molar to 0.020 molar phosphate, which is the most useful range for monitoring the effectiveness of the inhibitor with respect to aluminum. Table Vc gives the mean potentials of sensing electrodes 92 and 90 of steel and aluminum in volts versus reference electrode 94 of silver while Table Vd gives the same information using a reference electrode of SCE. Both solutions are the same as used in Tables Va and VB. Note the stability of the values as indicated by the plus or minus two standard deviations.

Table Vc

| phosphate concentration | mean potential, V | +2SD | −2SD |
| --- | --- | --- | --- |
| 0.000M | −0.568 | −0.210 | −0.926 |
| 0.005M | −0.549 | −0.471 | −0.627 |
| 0.010M | −0.564 | −0.442 | −0.686 |
| 0.020M | −0.510 | −0.370 | −0.650 |
| 0.035M | −0.440 | −0.316 | −0.564 |
| 0.070M | −0.234 | −0.134 | −0.334 |

Table Vd

| phosphate concentration | mean potential, V | +2SD | −2SD |
| --- | --- | --- | --- |
| 0.000M | −0.591 | −0.251 | −0.931 |
| 0.005M | −0.606 | −0.528 | −0.684 |
| 0.010M | −0.599 | −0.531 | −0.667 |
| 0.020M | −0.556 | −0.478 | −0.634 |
| 0.035M | −0.500 | −0.412 | −0.588 |
| 0.070M | −0.272 | −0.178 | −0.366 |

A review of Tables Vc and Vd shows no significant change in the potential of the sensing electrodes up to 0.10 molar and a consistent increase in potential form 0.020 molar to 0.070 molar covering the critical level of 0.035 molar. Thus, the dual sensing electrode is highly sensitive to the corrosivity of liquids to metals, particularly aluminum and its alloys.

The steel electrode, electrically coupled to the aluminum electrode, stabilizes the potential so that their combined potential remains steady in non-corrosive liquids (high concentrations of phosphate).

As indicated above with reference to sensor 30 (electrode 40) reference electrode 90 experiences no significant changes in potential in either corrosive or non-corrosive solutions, as shown in Table Ve, which gives the mean potentials of a silver electrode in volts versus an SCE electrode in the same coolant solution used for tables Va-Vd. Note the stability of the values as indicated by the plus or minus two standard deviations.

Table Ve

| phosphate concentration | mean potential, V | +2SD | −2SD |
| --- | --- | --- | --- |
| 0.000M | −0.020 | +0.072 | −0.112 |
| 0.005M | −0.059 | +0.013 | −0.131 |
| 0.010M | −0.031 | +0.073 | −0.135 |
| 0.020M | −0.044 | +0.054 | −0.142 |
| 0.035M | −0.059 | +0.023 | −0.141 |
| 0.070M | −0.037 | +0.019 | −0.093 |

While the above tables show the efficacy of the dual sensing electrode in typical coolant solutions in which the phosphate concentration is varied it is also known that differing concentrations of chloride affect the critical inhibitor concentration at which aluminum will start to corrode. In general, the more chloride included in the coolant solution, the higher the phosphate concentration required to protect the aluminum from corrosion. The chloride concentration can, for instance, vary due to different levels contained in tap water from one geographical location to another.

Tests similar to those conducted to obtain the data for tables Va-Ve were conducted using dual sensing electrodes of aluminum and steel versus a silver reference electrode in which the chloride concentration was varied as well as the phosphate concentration. In order to make the solutions consistent with most commercially available antifreeze compositions, 0.005 molar borate was added. A potential demarcation level of −0.4 volts was chosen for adjusting the alarm condition for the measuring circuit so that at each level of chloride concentration tested from 0 to 200 ppm a region A of conditions corrosive to aluminum in FIG. 6 was delineated from a region B of non-corrosive conditions. At the same time, samples of aluminum were placed in each solution to empirically determine which conditions were corrosive and which were not corrosive.

In each case the effect on the samples was consistent with the indication given by the sensor.

Figure 6:
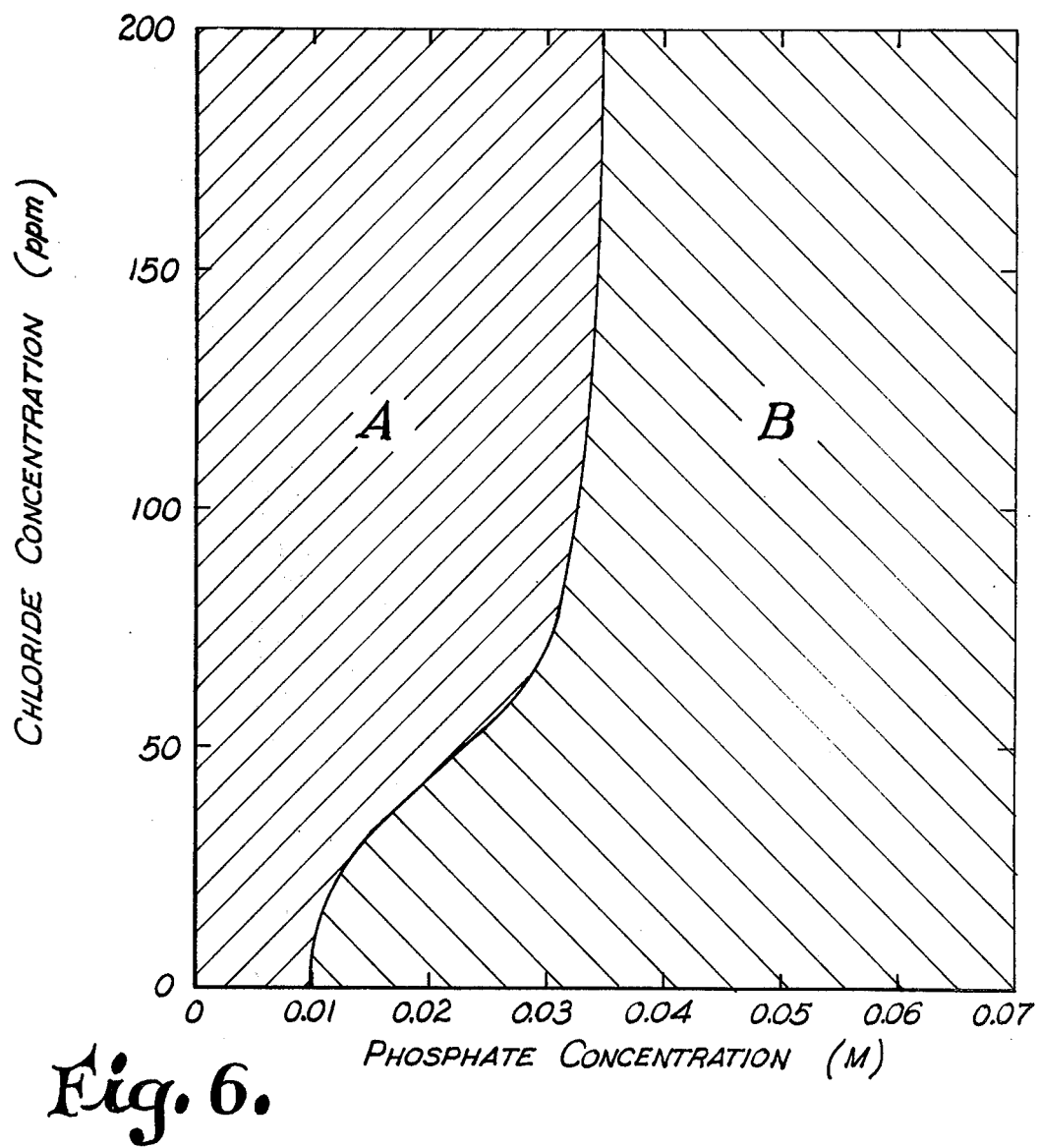
FIG. 6 is a graph of performance characteristics of a dual sensing electrode made in accordance with the invention for aluminum corrosion in typical coolant solutions.
Figure 7:
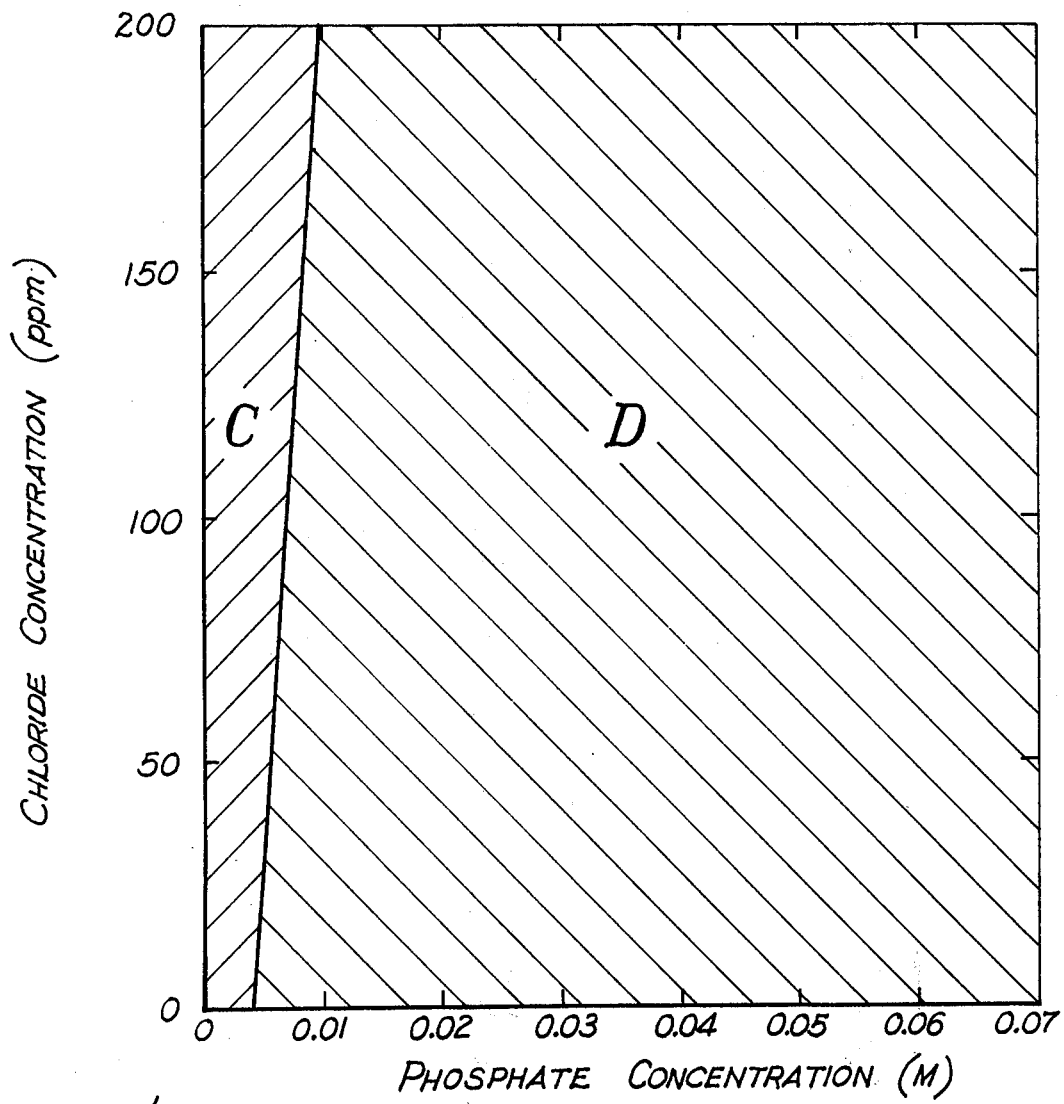
FIG. 7 is a graph similar to FIG. 6 of performance characteristics of a single sensing electrode for steel corrosion in typical coolant solution.

With reference to FIG. 7, by way of contrast, a similar series of tests was conducted using sensor 30 having a steel sensor electrode and a silver reference electrode in solutions of the same composition as those used for the tests resulting in FIG. 6. The measuring circuit was adjusted to indicate an alarm (corrosive) condition at −0.3 volts, suitable for steel. Region C of FIG. 7 corresponds to region A of FIG. 6 and represents those conditions for which sensor 30 indicates are corrosive while Region D corresponding to Region B of FIG. 6 represents those solution conditions which are non-corrosive. As stated supra, use of steel sensor electrode in sensor 30 is effective for conventional cooling system components including, iron, steel, copper and their alloys. However, it will be seen that while Region A overlaps Region C there are many conditions which are corrosive to aluminum for which sensor 30 would indicate to be non-corrosive.

Figure 8:
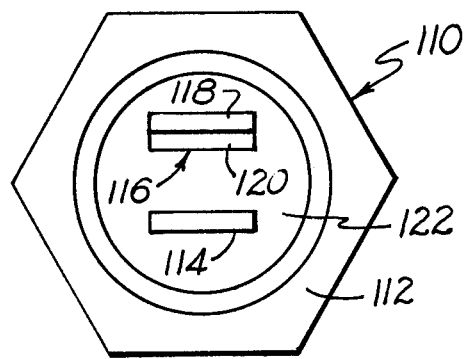
FIG. 8 is a rear view of another embodiment of a sensor made in accordance with the invention.

FIG. 8 shows a variation of the dual sensing electrodes, identified by numeral 110 and comprising a housing 112 mounting a reference electrode 114 of silver or other reference material described supra and a dual sensing electrode 116 comprising a clad element having a first layer 118 of steel bonded to a second layer 120 of aluminum mounted in housing 112 by electrically insulating potting material 122. The clad electrode is a convenient way of making the dual sensing electrode and is more conducive to mass production techniques.

Sensors made in accordance with the invention can of course be employed with liquids other than automotive coolants such as heat transfer liquids used in connection with solar energy systems or machine tools and the like. The measuring circuit can be adjusted to indicate an alarm condition at any given point so that a greater or lesser margin of safety may be maintained.

In the foregoing specification, the invention has been described with reference to specific exemplary embodiment thereof. However, it will be evident that various modifications and changes may be made thereunto without departing from the broader spirit and scope of the invention as set forth in the appended claims. The specification and drawings are, accordingly, to be regarded in an illustrative rather than a restrictive sense.

We claim:

1. Apparatus for monitoring the corrosivity of fluid, comprising reservoir defining means, a reference electrode mounted in and electrically isolated from the reservoir means and extending into the reservoir, a pair of sensing electrodes extending into said reservoir and composed of dissimilar materials wherein one of the materials is either steel or aluminum, said pair of sensing electrodes being physically electrically short circuited together and mounted in and electrically isolated from the reservoir defining means and the reference electrode, and high impedance voltage responsive means coupled across the reference and sensing electrodes respectively.

2. Apparatus for monitoring the corrosivity of fluid according to claim 1 in which said voltage responsive means includes indicating means which is actuated when the voltage level between the reference and sensing electrodes reaches a threshold value.

3. Apparatus for monitoring the corrosivity of fluid according to claim 1 in which the reference electrode is formed of silver.

4. Apparatus according to claim 1 in which said pair of sensing electrodes comprises a single clad element having layers of steel and aluminum bonded together.

5. A sensor adapted to be inserted in an aperture in a wall defining a reservoir, comprising a tubular member, a reference electrode and a pair of sensing electrodes extending through the member, one of the sensing electrodes composed of steel and the other of the sensing electrodes composed of aluminum, the sensing electrodes being electrically short circuited to one another by direct physical connection, and electrically insulative material mounting the electrodes in spaced relation to the member with the pair of sensing electrodes spaced from the reference electrode.

6. Apparatus according to claim 5 in which said pair of sensing electrodes comprises a single clad element having layers of steel and aluminum bonded together.

7. A vehicular cooling system including means for monitoring the effectiveness of corrosion inhibitor in coolant fluid, comprising a radiator, an engine block in which cooling passages were formed, means connecting the radiator to the cooling passages in the engine block in a closed system, means to circulate coolant fluid through the cooling system, an aperture formed in a wall defining the cooling system, a sensor received in the aperture, a reference electrode and a pair of sensing electrodes mounted in the sensor, the pair of sensing electrodes being composed of dissimilar materials wherein one material is either steel or aluminum, said pair of sensing electrodes being physically electrically connected in short circuit relation to one another and spaced from the reference electrode, at least a portion of each sensing electrode being adapted to come in contact with coolant fluid contained in the cooling system, and high impedance voltage responsive means coupled across the reference and sensing electrodes respectively.

8. A process for indicating when the corrosion inhibitor in vehicular cooling fluids becomes ineffective to prevent corrosion of the cooling system housing, including the steps of selecting a pair of sensing electrodes composed of dissimilar materials wherein one material is either steel or aluminum, disposing a reference electrode and said pair of sensing electrodes in contact with the cooling fluid, physically electrically coupling said pair of sensing electrodes together in short circuit relation and coupling high impedance voltage responsive means across the reference and sensing electrodes respectively for providing an output corresponding to the difference in potential between the reference and sensing electrodes.

9. A process according to claim 8 in which said reference electrode is composed of a standard reference electrode material and said pair of sensing electrodes are composed of aluminum and steel.

10. A sensor adapted to be inserted in an aperture in a wall defining a reservoir, comprising a tubular member, a reference electrode and a pair of sensing electrodes composed of dissimilar materials extending through the member, one of the sensing electrodes being composed of either steel or aluminum, the sensing electrodes being electrically short circuited to one another by direct physical connection, and electrically insulative material mounting the electrodes in spaced relation to the member with a pair of sensing electrodes spaced from the reference electrode.

* * * * *